(12) United States Patent
Hwang et al.

(10) Patent No.: US 12,162,018 B2
(45) Date of Patent: Dec. 10, 2024

(54) FOOD WASTE DISPOSER

(71) Applicant: SAMSUNG ELECTRONICS CO., LTD., Suwon-si (KR)

(72) Inventors: Yongjun Hwang, Suwon-si (KR); Keonpyo Koo, Suwon-si (KR); Kyoungmok Kim, Suwon-si (KR); Jiho Seo, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 268 days.

(21) Appl. No.: 17/662,045

(22) Filed: May 4, 2022

(65) Prior Publication Data
US 2023/0001422 A1 Jan. 5, 2023

Related U.S. Application Data

(63) Continuation of application No. PCT/KR2022/005635, filed on Apr. 20, 2022.

(30) Foreign Application Priority Data

Jul. 5, 2021 (KR) .......... 10-2021-0087931
Aug. 17, 2021 (KR) .......... 10-2021-0108087

(51) Int. Cl.
*B02C 18/16* (2006.01)
*A61L 9/014* (2006.01)
(Continued)

(52) U.S. Cl.
CPC .............. *B02C 18/16* (2013.01); *A61L 9/014* (2013.01); *A61L 11/00* (2013.01); *B01D 53/04* (2013.01);
(Continued)

(58) Field of Classification Search
CPC ..... B02C 18/16; B02C 18/0092; B02C 18/12; B02C 18/18; B02C 23/24;
(Continued)

(56) References Cited

U.S. PATENT DOCUMENTS 5,634,600 A 6/1997 Kubota et al.
10,906,046 B2 * 2/2021 Crepeau ................ C05F 17/907
2022/0001389 A1 * 1/2022 Maxwell ................ B02C 18/12

FOREIGN PATENT DOCUMENTS

JP H0914842 A 1/1997
JP 2002126696 A 5/2002
(Continued)

OTHER PUBLICATIONS

English translate (WO2010008164A2), retrieved date Mar. 4, 2024.*
(Continued)

*Primary Examiner* — Mohammed S. Alawadi

(57) ABSTRACT

Provided is a food waste disposer. The food waste disposer according to an embodiment of the disclosure includes: a housing; a grinder detachably installed inside the housing and configured to grind food waste accommodated therein; and a deodorizer positioned to a side of the grinder, and configured to suck a smell generated from the grinder and discharge the smell to outside of the housing, wherein the grinder includes: a grinding case; a rotating grinder including a plurality of blades rotatably installed at different heights inside the grinding case; and a wall grinder including a protrusion protruding inward from the grinding case at a different height from the plurality of blades, the wall grinder detachably installed on a side wall of the grinding case.

20 Claims, 14 Drawing Sheets

(51) Int. Cl.
  *A61L 11/00* (2006.01)
  *B01D 53/04* (2006.01)
  *B02C 18/00* (2006.01)
  *B02C 18/12* (2006.01)
  *B02C 18/18* (2006.01)
  *B02C 23/24* (2006.01)
  *B09B 3/35* (2022.01)
  *B09B 101/70* (2022.01)

(52) U.S. Cl.
  CPC .......... *B02C 18/0092* (2013.01); *B02C 18/12* (2013.01); *B02C 23/24* (2013.01); *B09B 3/35* (2022.01); *A61L 2209/14* (2013.01); *B01D 2253/102* (2013.01); *B01D 2257/90* (2013.01); *B09B 2101/70* (2022.01)

(58) Field of Classification Search
  CPC .......... B02C 2018/162; B02C 2201/066; A61L 9/014; A61L 11/00; A61L 2209/14; A61L 2209/22; B01D 53/04; B01D 2253/102; B01D 2257/90; B01D 2258/06; B01D 53/0407; B09B 3/35; B09B 2101/70
  See application file for complete search history.

(56) References Cited

FOREIGN PATENT DOCUMENTS

| | | | |
|---|---|---|---|
| JP | 2002346416 A | 12/2002 | |
| JP | 2003211120 A | 7/2003 | |
| JP | 2006055811 A | 3/2006 | |
| JP | 2010069425 A | 4/2010 | |
| JP | 2011036767 A | 2/2011 | |
| KR | 20090103066 A | 10/2009 | |
| KR | 20100008057 A | 1/2010 | |
| KR | 10-2011-0056078 A | 5/2011 | |
| KR | 20160044110 A | 4/2016 | |
| KR | 20160133903 A | 11/2016 | |
| KR | 10-2019-0000244 A | 1/2019 | |
| KR | 20190096629 A * | 8/2019 | |
| WO | WO-2010008164 A2 * | 1/2010 | ......... B02C 18/0084 |

OTHER PUBLICATIONS

English translate (KR20190096629A), retrieved date Mar. 4, 2024.*
International Search Report and Written Opinion of the International Searching Authority dated Aug. 8, 2022, in connection with International Application No. PCT/KR2022/005635, 11 pages.

* cited by examiner

FOOD WASTE DISPOSER

CROSS-REFERENCE TO RELATED APPLICATION

This application is a continuation of International Application No. PCT/KR2022/005635, filed Apr. 20, 2022, which is based on and claims priority to Korean Patent Applications No. 10-2021-0087931, filed on Jul. 5, 2021, and No. 10-2021-0108087, filed on Aug. 17, 2021, in the Korean Intellectual Property Office, the disclosures of which are incorporated by reference herein in their entireties.

BACKGROUND

1. Field

The disclosure relates to a food waste disposer, and more particularly, to a food waste disposer with an improved structure.

2. Description of the Related Art

In general, a food waste disposer is an apparatus for processing food waste by drying, stirring, and grinding the food waste. The food waste disposer includes a grinding device for stirring and grinding food waste. Also, the food waste disposer includes a heater for applying heat to the grinding device to dry food waste contained in the grinding device.

The grinding device includes a grinding case used as a container in which food waste is stored, and a grinder which is rotatable inside the grinding case.

However, when the grinder stirs and grinds food waste contained in the grinding case, the food waste tends to move gradually to the inner side wall of the grinding case.

The food waste moved to the inner side wall of the grinding case is clumped together, which may deteriorate the grinding performance of the food waste disposer. Also, the clumped food waste may interfere with rotations of the grinder, which may overload the driving motor of the grinder.

SUMMARY

Therefore, it is an aspect of the disclosure to provide a food waste disposer having a compact layout.

It is another aspect of the disclosure to provide a food waste disposer having a compact size and capable of improving grinding performance of a grinder.

Additional aspects of the disclosure will be set forth in part in the description which follows and, in part, will be obvious from the description, or may be learned by practice of the disclosure.

A food waste disposer according to a concept of the disclosure includes: a housing; a grinder detachably installed inside the housing and configured to grind food waste accommodated therein; and a deodorizer positioned to a side of the grinder, and configured to suck a smell generated from the grinder and discharge the smell to outside of the housing, wherein the grinder includes: a grinding case; a rotating grinder including a plurality of blades rotatably installed at different heights inside the grinding case; and a wall grinder including a protrusion protruding inward from the grinding case at a different height from the plurality of blades, the wall grinder detachably installed on a side wall of the grinding case.

The rotating grinder may include: a center body installed at a center of the grinding case and receiving power; and a first blade extending toward the side wall of the grinding case from the center body, wherein the first blade includes a grinding portion extending in parallel to the side wall of the grinding case and configured to separate food waste stacked on the side wall.

The grinding portion may be a first grinding portion, and the first blade may further include a second grinding portion connected to the first grinding portion and extending horizontally with respect to a bottom plate of the grinding case.

The rotating grinder may further include a second blade curved from the center body and extending toward the side wall of the grinding case.

The second blade may include a blade chamfer inclined with respect to a rotation direction of the rotating grinder.

The rotating grinder may include a third blade extending from the center body toward the side wall of the grinding case, and including an uneven portion formed at a lower side of the third blade to rake out food waste existing on a bottom plate of the grinding case.

The wall grinder may further include a chamfer formed at an outer surface of the protrusion in such a way as to be inclined with respect to the outer surface of the protrusion.

The rotating grinder may include: a first blade including a grinding portion extending in parallel to the side wall of the grinding case; a second blade curved and extending along a rotation direction of the rotating grinder; and a third blade formed at a lower location than the second blade.

The wall grinder may include: a first protrusion positioned between the first blade and the second blade; and a second protrusion positioned between the second blade and the third blade.

The food waste disposer may further include: an upper frame positioned in an upper portion of the housing and including an opening in which the grinder is inserted; and a housing cover rotatably coupled with one side of the upper frame and opening or closing the opening.

The upper frame may include: a base forming an upper surface; and an inlet protruding upward from the base and accommodating a portion of the deodorizer, wherein a communicating hole communicating with the grinder is formed in the inlet.

The deodorizer may include: a communicating case of which a portion is accommodated in the inlet, the communicating case positioned behind the grinder; and a fan installing case connected to the communicating case, and accommodating a circulating fan forming a suction airflow toward the communicating case from the grinder.

The deodorizer may include: a filter configured to filter air sucked from the grinder; and an exhaust case installed in one side of the filter and communicating with an exhaust hole of the housing, wherein air filtered by the filter flows along the exhaust case.

The food waste disposer may further include: a bottom frame positioned below the upper frame and on which the grinder is seated; and a heater positioned between the bottom frame and the grinder, and configured to heat the grinder.

The food waste disposer may further include a food waste bin positioned below the grinder to store food waste grinded by the grinder and transferred from the grinder.

A food waste disposer according to another concept of the disclosure includes: a housing including an exhaust hole; a grinder detachably installed inside the housing and configured to grind food waste accommodated therein; a deodorizer positioned behind the grinder and configured to suck a smell generated from the grinder and discharge the smell through the exhaust hole of the housing; and an upper frame positioned in an upper portion of the housing and including an opening accommodating the grinder and an inlet accommodating a portion of the deodorizer, wherein the grinder includes a grinding case accommodating food waste therein and a rotating grinder rotatably provided inside the grinding case, wherein the rotating grinder includes a blade in which a grinding portion extending in parallel to a side wall of the grinding case is formed to separate food waste from the side wall of the grinding case.

The blade may be a first blade, and the rotating grinder may include a second blade formed at a lower height than the first blade, and a third blade formed at a lower height than the second blade and including an uneven portion formed toward a bottom plate of the grinding case.

The food waste disposer may further include a wall grinder detachably installed on the side wall of the grinding case, and including a protrusion formed at a different height from the first blade, the second blade, and the third blade and extending toward inside of the grinding case.

A food waste disposer according to another concept of the disclosure includes: a housing; a housing cover opening or closing an upper side of the housing; a grinder including a grinding case installed inside the housing and configured to grind food waste and a blade including a grinding portion extending in parallel to a side wall of the grinding case; a deodorizer positioned behind the grinder and configured to suck a smell generated from the grinder and filter the smell; and a food waste bin positioned below the grinder and storing grinded food waste.

The food waste disposer may further include an opening formed in an upper portion of the housing and accommodating the grinder; and an upper frame formed to one side of the opening and including an inlet communicating the deodorizer with the grinder.

Before undertaking the detailed description below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
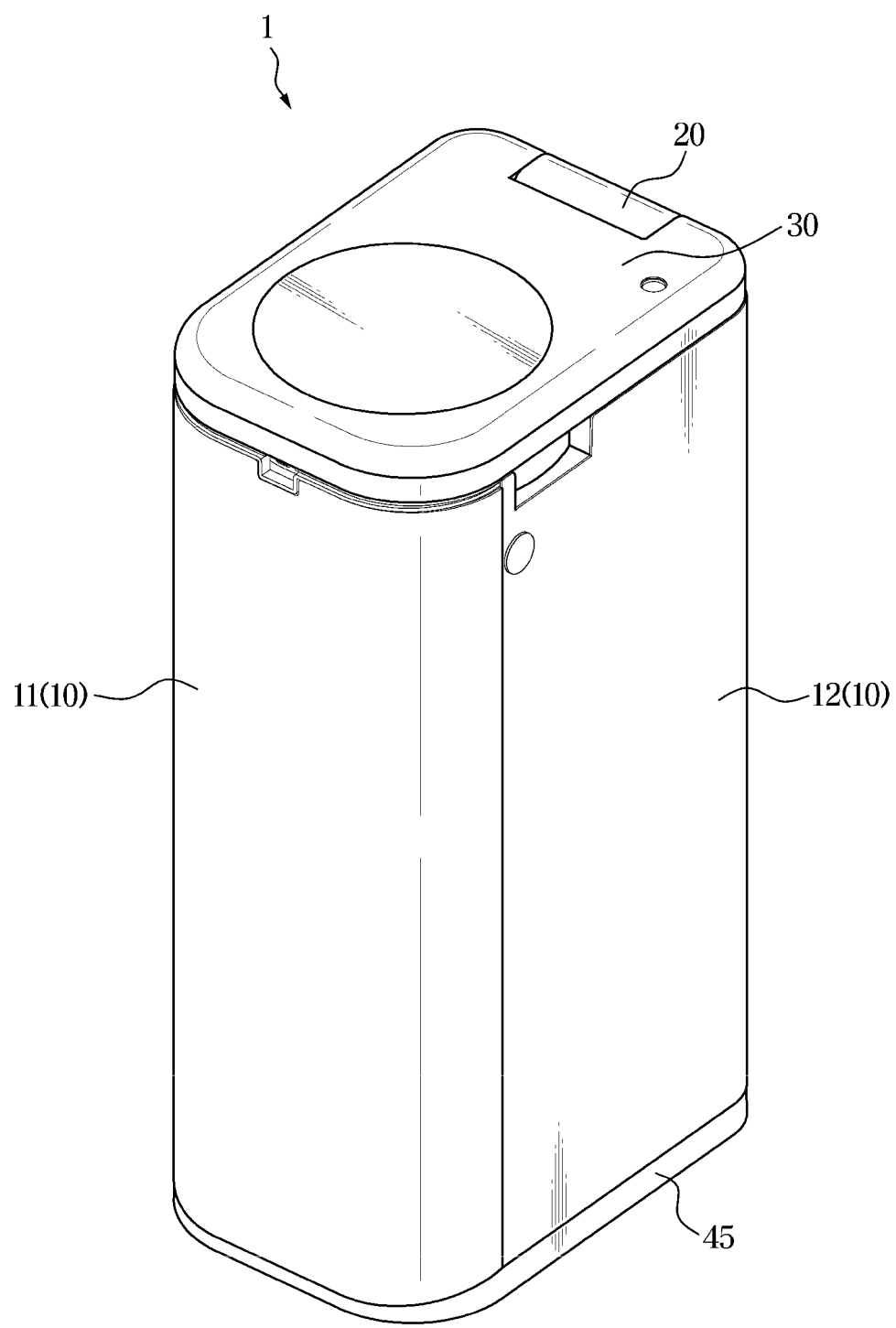
FIG. 1 is a perspective view of a food waste disposer according to various embodiments of the disclosure.

FIGS. 1 through 14, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Configurations illustrated in the embodiments and the drawings described in the present specification are only the preferred embodiments of the disclosure, and thus it is to be understood that various modified examples, which may replace the embodiments and the drawings described in the present specification, are possible when filing the present application.

Also, like reference numerals or symbols denoted in the drawings of the present specification represent members or components that perform the substantially same functions.

Also, the terms used in the present specification are merely used to describe embodiments, and are not intended to restrict and/or limit the disclosure. It is to be understood that the singular forms "a," "an," and "the" include plural referents unless the context clearly dictates otherwise. It will be understood that when the terms "includes," "comprises," "including," and/or "comprising," when used in this specification, specify the presence of stated features, figures, steps, operations, components, members, or combinations thereof, but do not preclude the presence or addition of one or more other features, figures, steps, operations, components, members, or combinations thereof.

It will be understood that, although the terms including ordinal numbers, such as "first", "second", etc., may be used herein to describe various components, these components should not be limited by these terms. These terms are only used to distinguish one component from another. For example, a first component could be termed a second component, and, similarly, a second component could be termed a first component, without departing from the scope of the disclosure. As used herein, the term "and/or" includes any and all combinations of one or more of associated listed items.

Throughout the disclosure, the expression "at least one of a, b or c" indicates only a, only b, only c, both a and b, both a and c, both b and c, all of a, b, and c, or variations thereof.

Hereinafter, embodiments of the disclosure will be described in detail with reference to the accompanying drawings.

Figure 2:
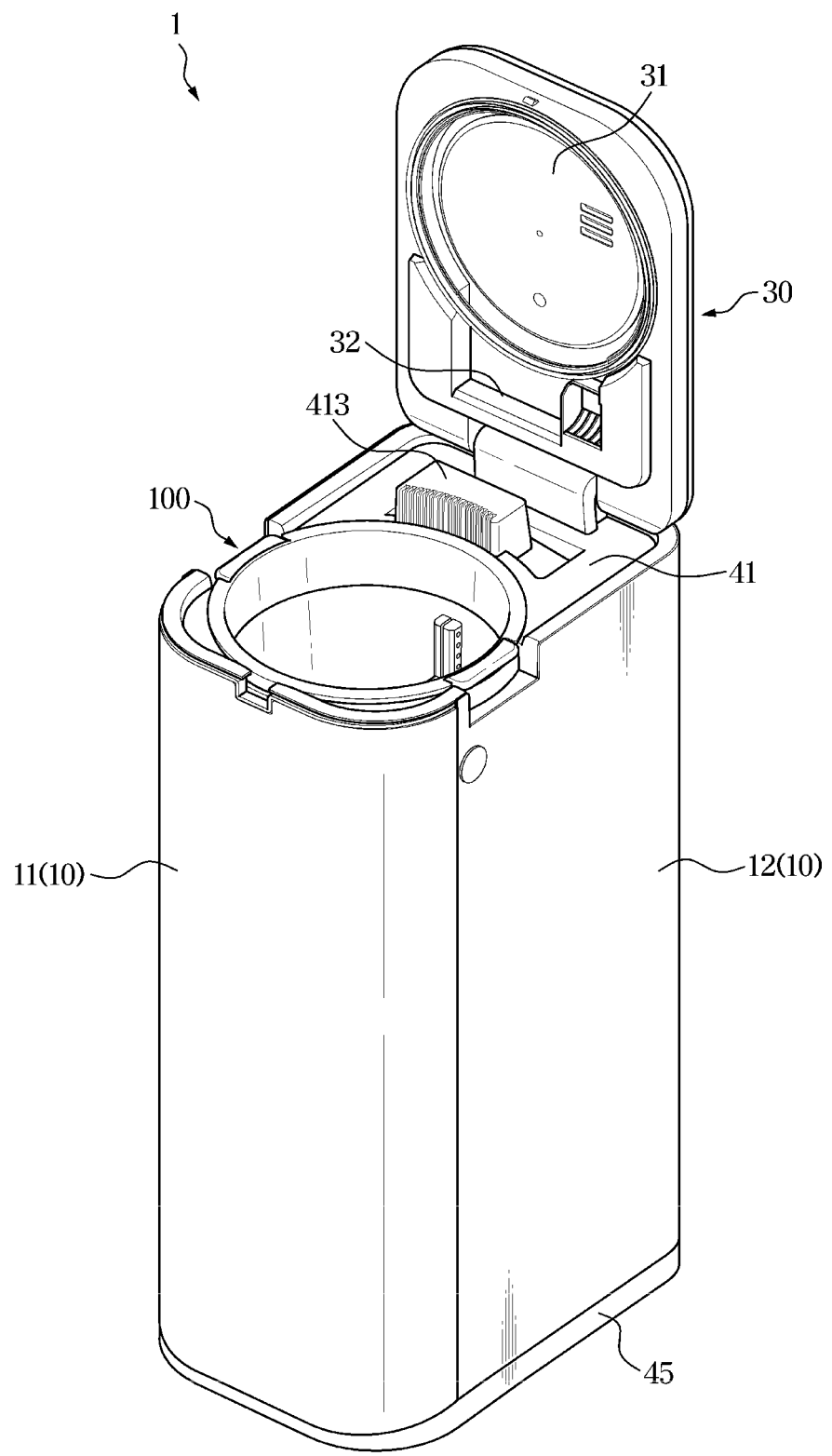
FIG. 2 is a perspective view showing an open state of a housing cover in the food waste disposer of FIG. 1.
Figure 3:
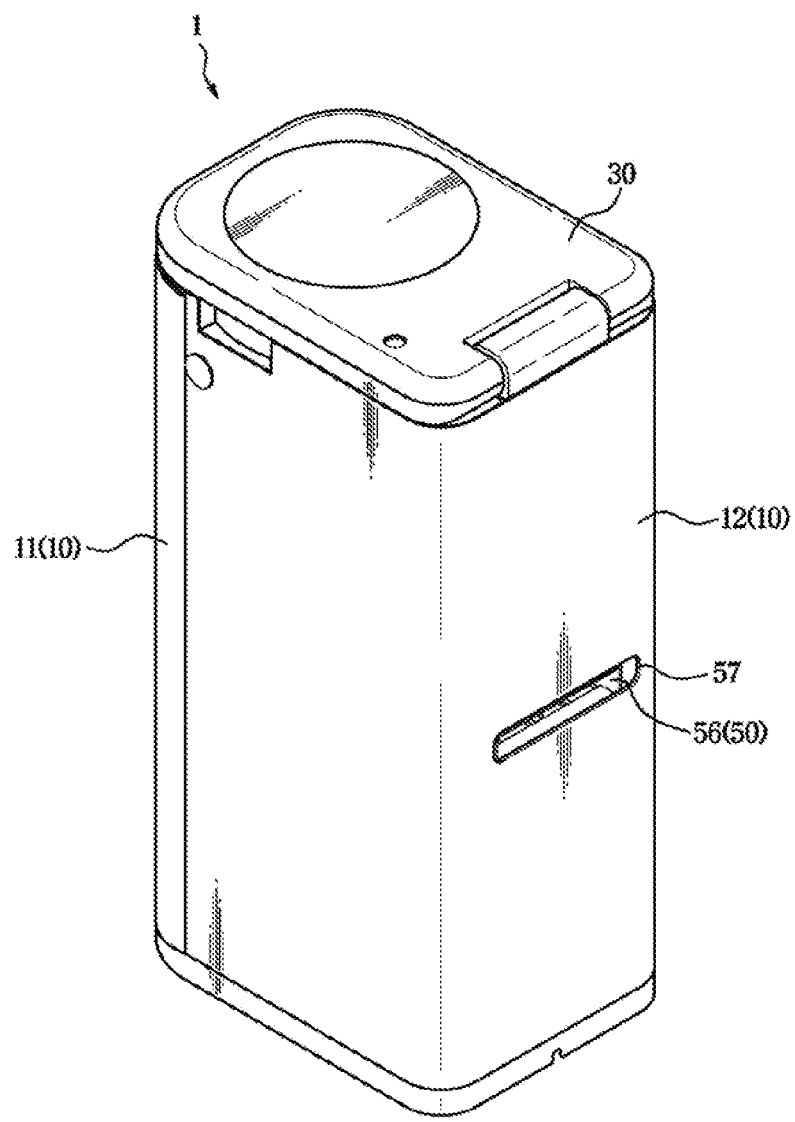
FIG. 3 is a perspective view showing a rear side of the food waste disposer of FIG. 1.

FIG. 1 is a perspective view of a food waste disposer 1 according to various embodiments of the disclosure. FIG. 2 is a perspective view showing an open state of a housing cover 30 in the food waste disposer 1 of FIG. 1. FIG. 3 is a perspective view showing a rear side of the food waste disposer 1 of FIG. 1.

Referring to FIGS. 1 to 3, a food waste disposer 1 according to various embodiments of the disclosure may include a housing 10 forming an outer appearance or exterior, and a housing cover 30 for opening or closing an upper side of the housing 10.

The housing cover 30 may be rotatable with respect to the housing 10 through a hinge 20.

The housing 10 may include a front housing 11 and a rear housing 12. The front housing 11 may form a front outer appearance or front exterior of the food waste disposer 1. The rear housing 12 may form a rear outer appearance or rear exterior of the food waste disposer 1.

The front housing 11 and the rear housing 12 may be mounted on a base frame 45 forming a bottom of the food waste disposer 1.

The front housing 11 may be detachable from the rear housing 12. Accordingly, a user may separate the front housing 11 from the rear housing 12 to access various components installed inside the food waste disposer 1.

The housing cover 30 may include a grinder cover 31 and an upper frame receiver 32.

The grinder cover 31 may be positioned in a front portion of the housing cover 30 to open and close an open upper side of a grinder 100.

The upper frame receiver 32 may be positioned behind the grinder cover 31. The upper frame receiver 32 may accommodate a portion of an inlet 413 of an upper frame 41 which will be described below. Accordingly, the upper frame receiver 32 may be depressed inward from the housing cover 30.

The grinder 100 may be installed inside the housing 10. More specifically, the grinder 100 may pass through a front portion of the upper frame 41 and be accommodated in the housing 10. Details about this will be described below.

The rear housing 12 may include an exhaust hole 57. The exhaust hole 57 may communicate with an exhaust case 56 of a deodorizer 50 which will be described below. The deodorizer 50 may suck bad smells from the grinder 100, filter the bad smells, and then discharge the filtered air to outside. At this time, the filtered air may be discharged to the outside through the exhaust hole 57 of the rear housing 12.

Figure 4:
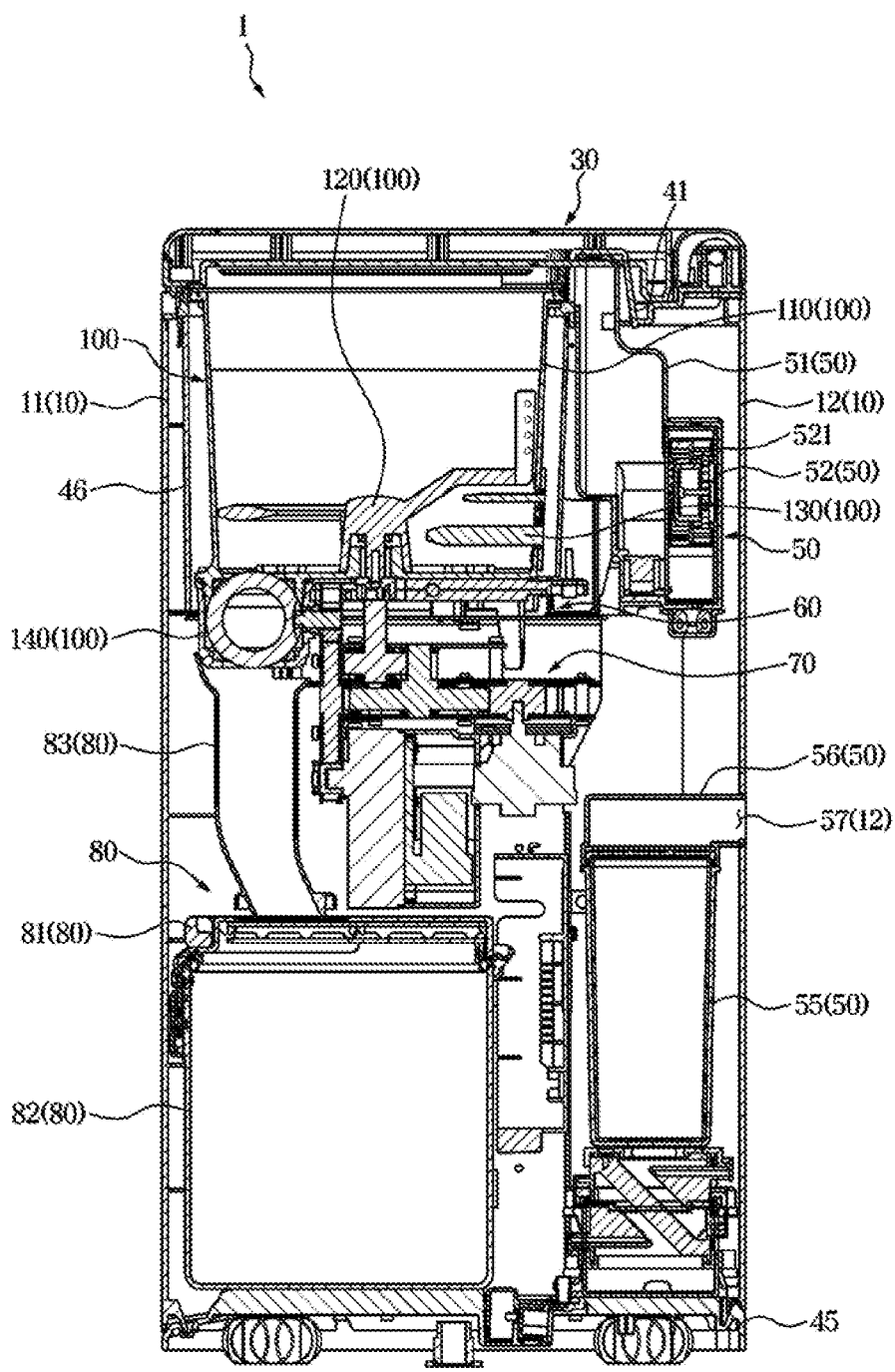
FIG. 4 is a cross-sectional view of the food waste disposer of FIG. 1.

FIG. 4 is a cross-sectional view of the food waste disposer of FIG. 1.

Referring to FIG. 4, the food waste disposer 1 may include the grinder 100 positioned in a front upper portion. The grinder 100 may be positioned below the housing cover 30. The housing cover 30 may open and close the open upper side of the grinder 100. Alternatively, the housing cover 30 may open and close the upper side of the housing 10.

The food waste disposer 1 may include a heater 60.

The heater 60 may be positioned below the grinder 100 and heat the grinder 100. More specifically, the heater 60 may include a heating wire accommodating frame accommodating a heating wire therein. The heating wire accommodating frame may be positioned below a grinding case 110 of the grinder 100.

The grinder 100 may be positioned inside an accommodating frame 46 fixed inside the housing 10. Also, the heater 60 may be positioned inside the accommodating frame 46.

The accommodating frame 46 may cover outer sides of the grinder 100 and the heater 60 such that the grinder 100 and the heater 60 are more stably supported and accommodated inside the food waste disposer 1.

The food waste disposer 1 may include a driver 70.

The driver 70 may be positioned below the grinder 100 and the heater 60. The driver 70 may transfer power to the grinder 100.

More specifically, the driver 70 may transfer power to a rotating grinder 120 (which will be described below) of the grinder 100 and to a valve assembly 140 of the grinder 100.

The driver 70 may be supported at both sides by a side frame 44, which will be described below, and be fixed to a lower portion of the grinder 100.

The food waste disposer 1 may include the deodorizer 50.

The deodorizer 50 may suck bad smells, etc. generated from the grinder 100. Bad smells sucked into the deodorizer 50 may be filtered and then discharged to outside of the food waste disposer 1.

More specifically, the deodorizer 50 may suck smells from above the grinder 100. Accordingly, the deodorizer 50 may be positioned behind the grinder 100.

The food waste disposer 1 may include a food waste bin 80.

The food waste bin 80 may store food waste dried and grinded by the grinder 100 and transferred from the grinder 100.

More specifically, the food waste bin 80 may include a transfer duct 83 connected to the valve assembly 140 of the grinder 100.

The valve assembly 140 of the grinder 100 may open and close an outlet 114 (see FIG. 8) of the grinder 100.

In a case in which the valve assembly 140 opens the outlet 114 of the grinding case 110, grinded food waste existing inside the grinding case 110 may be transferred to a storage case 82 of the food waste bin 80 through the transfer duct 83.

Figure 5:
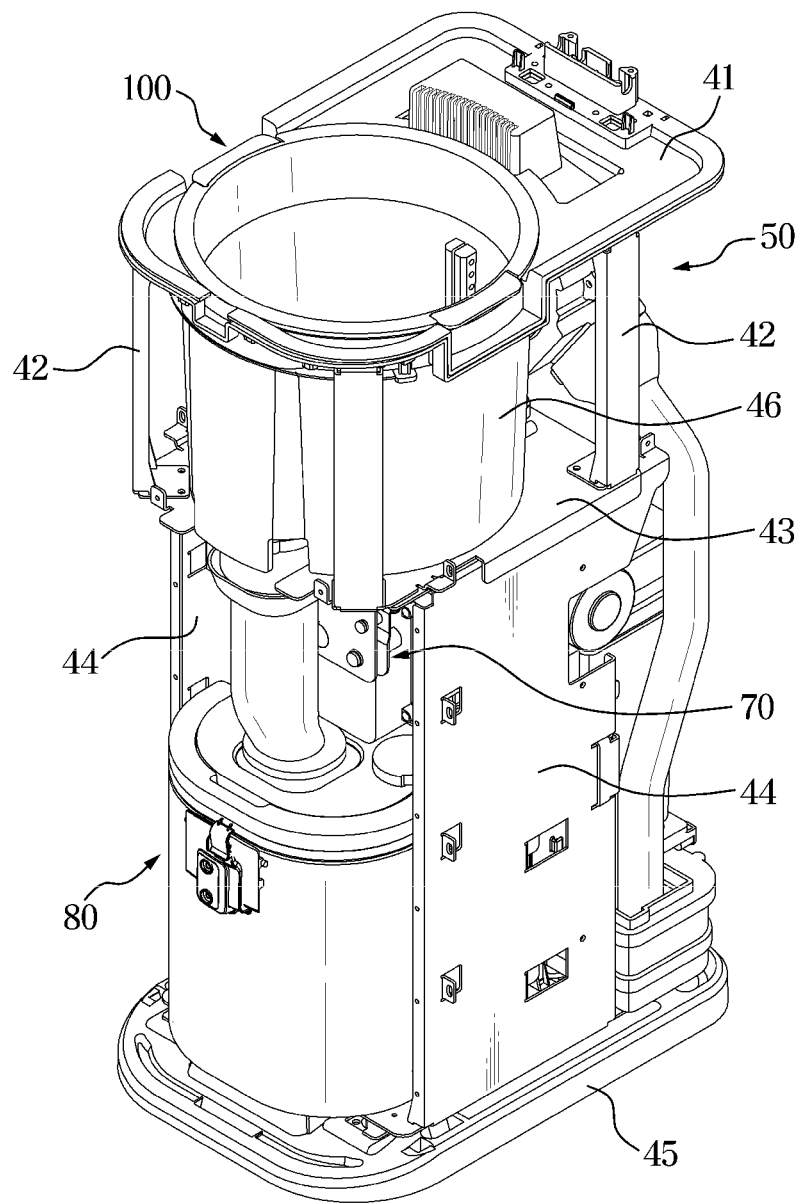
FIG. 5 is a perspective view showing a food waste disposer according to various embodiments of the disclosure, after a housing and a housing cover are removed from the food waste disposer.
Figure 6:
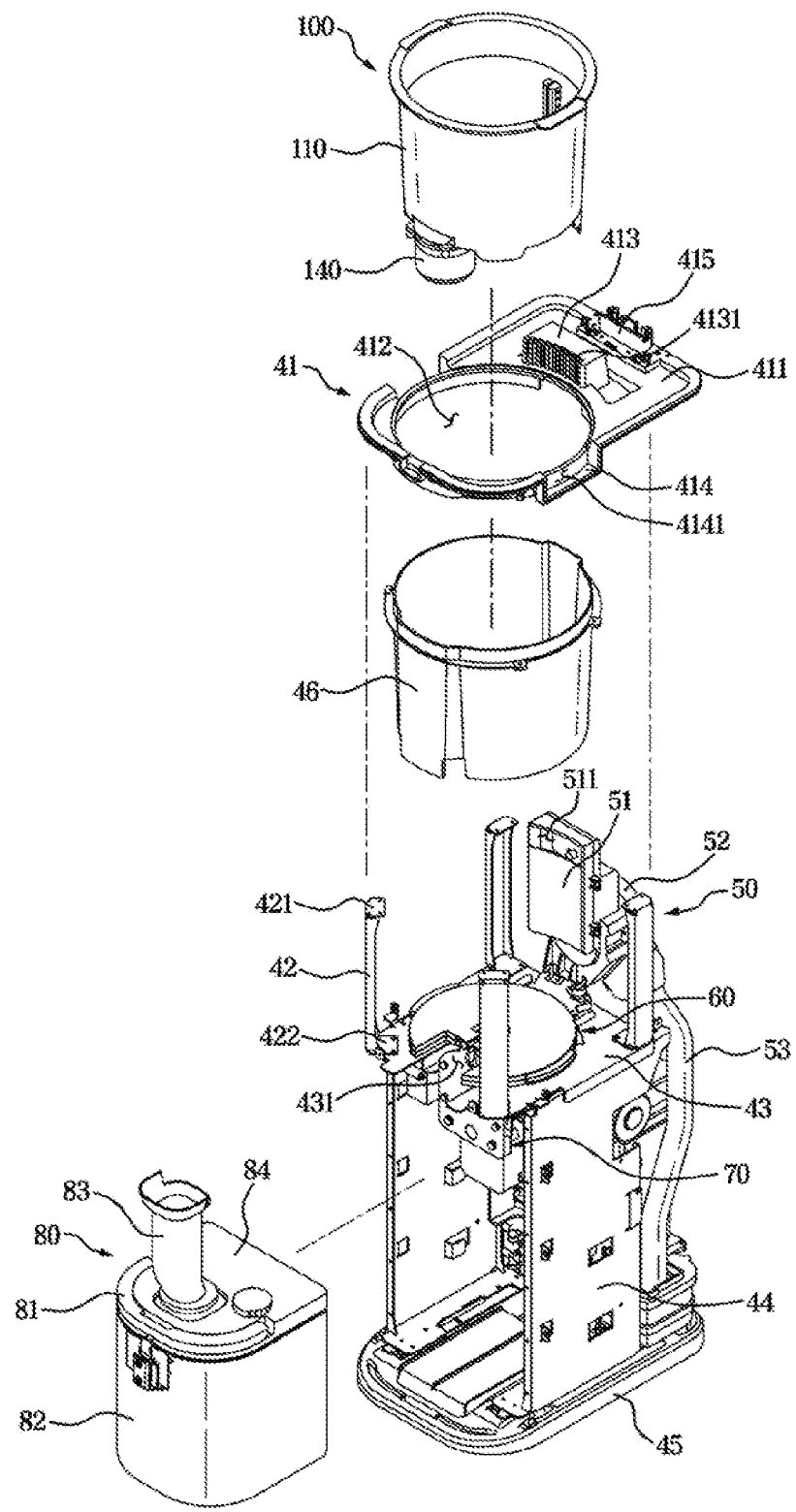
FIG. 6 is an exploded perspective view of the food waste disposer of FIG. 5.
Figure 7:
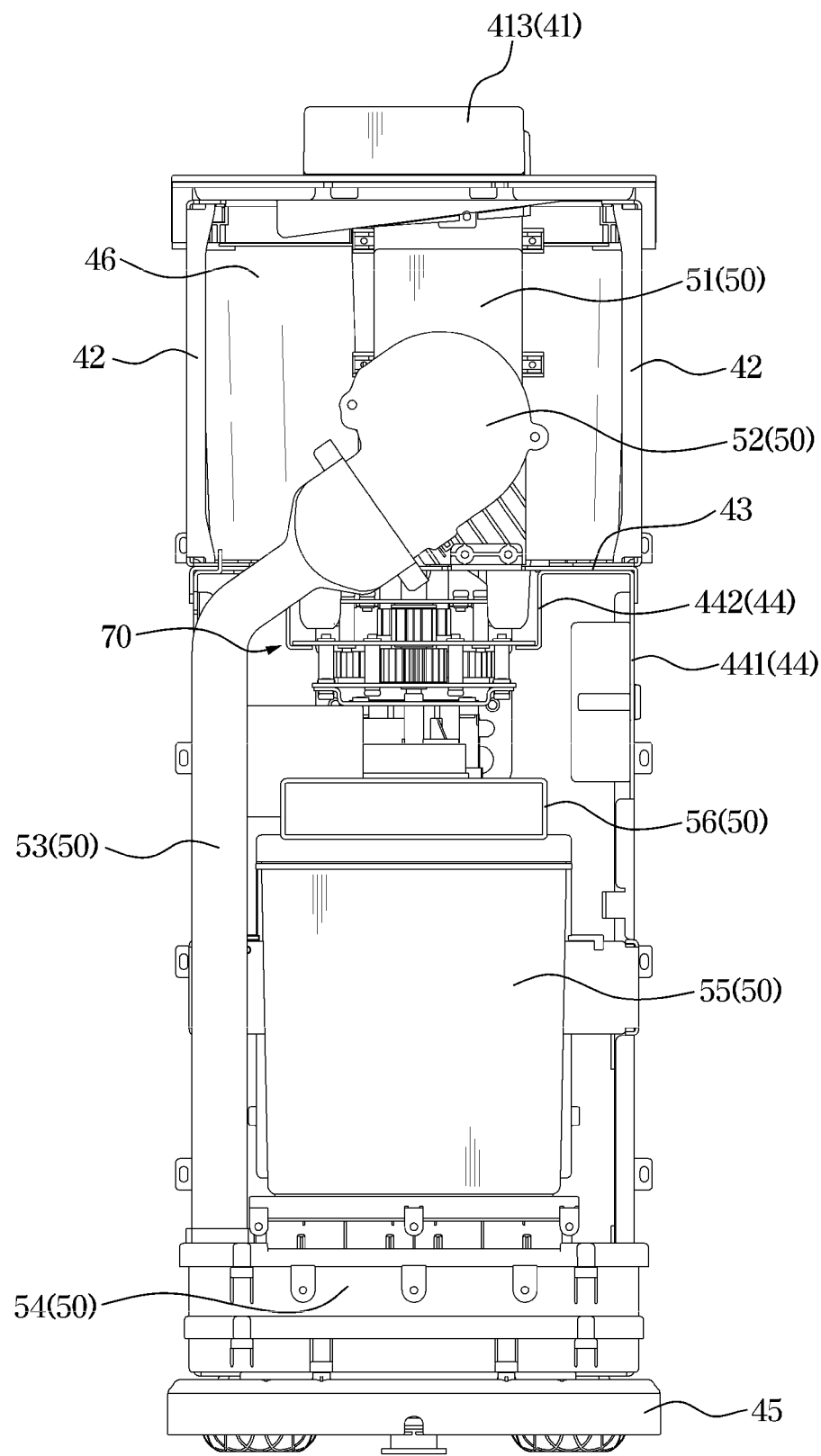
FIG. 7 shows a rear side of the food waste disposer of FIG. 5.

FIG. 5 is a perspective view showing a food waste disposer according to various embodiments of the disclosure, after a housing and a housing cover are removed from the food waste disposer. FIG. 6 is an exploded perspective view of the food waste disposer of FIG. 5. FIG. 7 shows a rear side of the food waste disposer of FIG. 5.

Referring to FIGS. 5 to 7, the food waste disposer 1 according to various embodiments of the disclosure may include a plurality of frames for supporting the grinder 100, the deodorizer 50, the food waste bin 80, the driver 70, etc.

The food waste disposer 1 may include the upper frame 41. The grinder 100 may be inserted in the front portion of the upper frame 41.

The upper frame 41 may include a base 411. The base 411 may form an upper surface of the upper frame 41.

The upper frame 41 may include an opening 412 formed in front of the base 411. The grinder 100 may be separated from the housing 10 through the opening 412. Also, the opening 412 may have a size corresponding to the open upper side of the grinder 100.

Accordingly, a user may put food waste into the inside of the grinder 100 through the opening 412. That is, the opening 412 may be provided as an entrance. The housing cover 30 may open and close the opening 412 of the upper frame 41.

The upper frame 41 may include the inlet 413 positioned behind the opening 412. The inlet 413 may protrude upward from the base 411 of the upper frame 41.

The inlet 413 may accommodate a portion of the deodorizer 50. More specifically, an upper portion of a communicating case 51 (will be described below) of the deodorizer 50 may be accommodated in the inlet 413.

A communicating hole 4131 communicating with the grinder 100 may be formed in the inlet 413 of the upper frame 41. A plurality of communicating holes 4131 may be provided.

Accordingly, inside air of the grinder 100 may flow to the inlet 413 through the communicating hole 4131 of the upper frame 41 by a suction force generated by the deodorizer 50, and the air entered the inlet 413 may flow to inside of the communicating case 51 of the deodorizer 50. Details about this will be described below.

The upper frame 41 may include a depressed portion 414 at both sides. The depressed portion 414 may be bent downward from the base 411 of the upper frame 41. The depressed portion 414 may form a grip space 4141 therein.

Accordingly, a handle 113 (see FIG. 8) of the grinder 100 may be positioned on the depressed portion 414 to enable a user to easily grip the handle 113 to separate the grinder 100 from the housing 10.

The upper frame 41 may include a hinge installing portion 415 at a rear portion. The hinge 20 shown in FIG. 1 may be installed in the hinge installing portion 415. Accordingly, the housing cover 30 may be rotatably coupled with the upper frame 41 through the hinge 20.

The food waste disposer 1 may include the accommodating frame 46.

The accommodating frame 46 may accommodate the grinder 100 therein. The accommodating frame 46 may be positioned below the upper frame 41.

The accommodating frame 46 may be substantially formed in a shape of a cylinder of which upper and lower sides open.

The food waste disposer 1 may include a bottom frame 43.

The accommodating frame 46 may be mounted on the bottom frame 43. The heater 60 may be mounted on an upper surface of the bottom frame 43. An incision portion 431 may be formed in a front portion of the bottom frame 43.

Accordingly, the grinding case 110 of the grinder 100 may be positioned on the upper surface of the heater 60, and the valve assembly 140 protruding downward from the grinder 100 may penetrate the bottom frame 43 to be positioned in front of the bottom frame 43.

The food waste disposer 1 may include a support frame 42. A plurality of support frames 42 may be provided to support the upper frame 41. In FIG. 6, four support frames 42 are shown, however, the number of the support frames 42 is not limited to four.

The support frame 42 may include an upper supporter 421 provided at an upper portion of the support frame 42 and supporting the upper frame 41. Also, the support frame 42 may include a bottom installing portion 422 provided at a lower portion of the support frame 42 and installed on the bottom frame 43.

The support frame 42 may be substantially formed in a shape of a bar, and support the upper frame 41 while occupying a small space.

The food waste disposer 1 may include the side frame 44 and the base frame 45 forming the bottom of the food waste disposer 1. A pair of side frames 44 may be provided.

The side frames 44 may be positioned respectively at both sides of a lower surface of the bottom frame 43. The side frames 44 may be positioned between the bottom frame 43 and the base frame 45.

Each side frames 44 may include a side body 441 covering side portion of the food waste bin 80.

The side frame 44 may include a driver supporter 442 bent inward from the side body 441 and coupled with the bottom frame 43.

The food waste bin 80 may receive dried and grinded food waste from the grinder 100 through the transfer duct 83. The food waste bin 80 may include the storage case 82. The storage case 82 may be connected to the transfer duct 83 and store grinded food waste.

The food waste bin 80 may include a case cover 84 provided at an upper portion of the storage case 82. A grip portion 81 that may be gripped may be installed in a front portion of the case cover 84.

The deodorizer 50 may include the communicating case 51.

The communicating case 51 may be positioned behind the grinder 100. More specifically, an upper portion of the communicating case 51 may be accommodated in the inlet 413 of the upper frame 41.

The communicating case 51 may include an inlet hole 511 formed by cutting a front side of the communicating case 51. Water, bad smell, etc. generated in the inside of the grinder 100 may enter the communicating hole 4131 formed in the inlet 413 of the upper frame 41 and the inlet hole 511 of the communicating case 51.

The deodorizer 50 may include a fan installing case 52.

The fan installing case 52 may be connected to the communicating case 51. The fan installing case 52 may form a suction airflow toward the communicating case 51 from the grinder 100.

A blow fan 521 may be positioned inside the fan installing case 52 to generate a suction force.

The deodorizer 50 may include a deodorizing duct 53.

The deodorizing duct 53 may be connected to the fan installing case 52. The deodorizing duct 53 may form a path along which air entered the fan installing case 52 flows.

The deodorizer 50 may include a duct installing frame 54 and a filter 55.

The duct installing frame 54 may be connected to the deodorizing duct 53. The filter 55 may be installed on the duct installing frame 54.

A deodorizing filter made of activated carbon, etc. may be positioned inside the filter 55 to filter polluted air generated in the grinder 100. The filter 55 may include a filter case.

The deodorizer 50 may include an exhaust case 56.

The exhaust case 56 may be installed on one side of the filter 55 to cause air filtered by the filter 55 to flow. More specifically, the exhaust case 56 may be installed on an upper side of the filter 55.

Accordingly, the filtered air may communicate with the exhaust hole 121 of the rear housing 12 through the exhaust case 56 and then be discharged to the outside.

Figure 8:
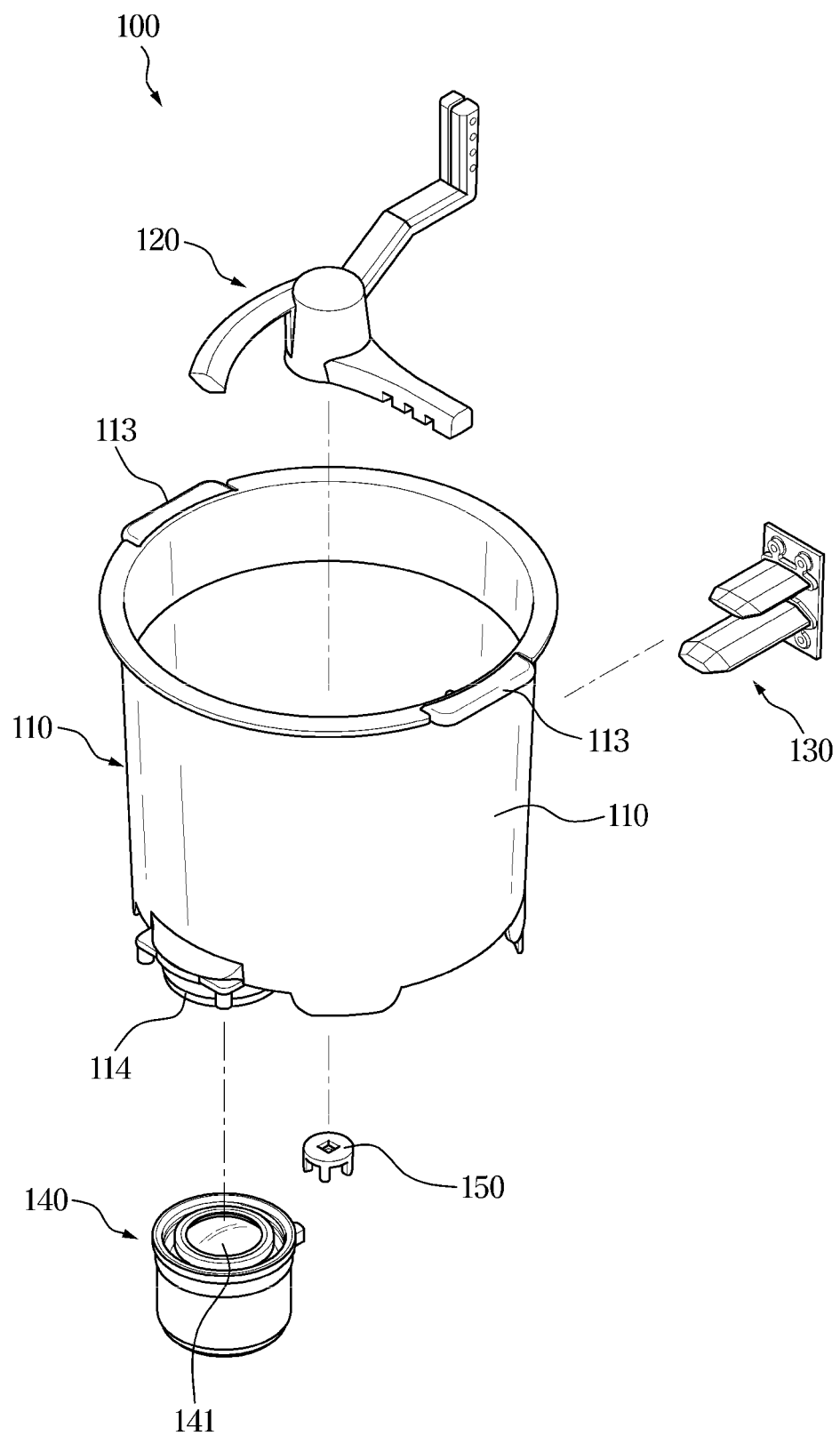
FIG. 8 is an exploded perspective view of a grinder in the food waste disposer of FIG. 6.

FIG. 8 is an exploded perspective view of a grinder in the food waste disposer of FIG. 6.

Referring to FIG. 8, the grinder 100 may include the grinding case 110, and the rotating grinder 120 that is rotatable inside the grinding case 110.

The grinding case 110 may accommodate food waste therein. Food waste accommodated in the grinding case 110 may be dried, stirred, and grinded.

The grinding case 110 may be substantially formed in a shape of a cylinder of which an upper side opens.

The grinding case 110 may include a pair of handles 113. The pair of handles 113 may be provided at both sides of an upper end of the grinding case 110. The pair of handles 113 may protrude outward from the grinding case 110 to enable a user to grip the pair of handles 113.

The rotating grinder 120 may rotate by receiving power from inside of the grinding case 110. More specifically, the rotating grinder 120 may be coupled with a power transfer member 150 and power generated by the driver 70 may be transferred to the power transfer member 150 to rotate the rotating grinder 120.

The grinder 100 may include a wall grinder 130.

The wall grinder 130 may be inserted into the inside of the grinding case 110 from outside of the grinding case 110. More specifically, the wall grinder 130 may be installed outside the grinding case 110 and protrude to the inside of the grinding case 110.

The wall grinder 130 may interwork with the rotating grinder 120 to grind food waste existing inside the grinding case 110. Details about this will be described below.

The grinder 100 may include the valve assembly 140.

The valve assembly 140 may be positioned below the grinding case 110. The valve assembly 140 may open and close an outlet 114 (see FIG. 11) formed in a bottom plate 112 of the grinding case 110.

Through the outlet 114 opened by the valve assembly 140, grinded food waste existing inside the grinding case 110 may be transferred to the food waste bin 80. Accordingly, the valve assembly 140 may be connected to the transfer duct 83 in such a way as to communicate with the transfer duct 83.

The valve assembly 140 may include a valve member 141. The valve member 141 may be a ball valve. Accordingly, the valve member 141 may rotate to open and close the outlet 114 of the grinding case 110.

In FIG. 8, the valve assembly 140 is shown to be a separate configuration, however, the valve assembly 140 and the grinding case 110 may be integrated into one body.

Figure 9:
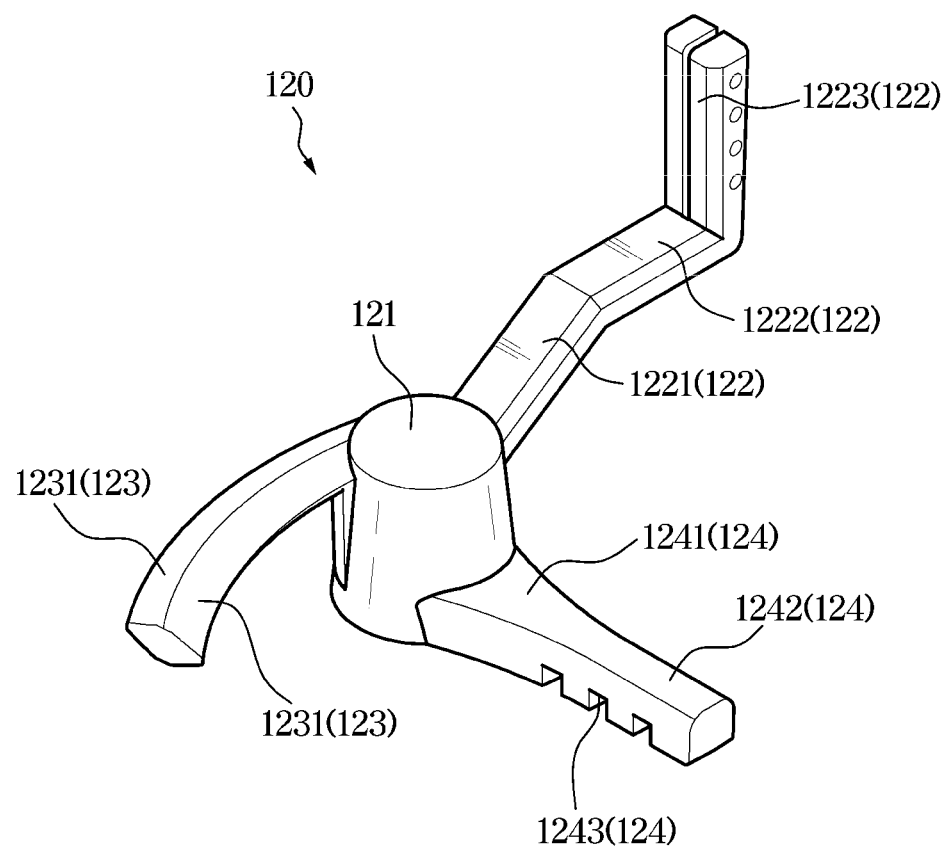
FIG. 9 shows a rotating grinder of the grinder of FIG. 8.

FIG. 9 shows a rotating grinder of the grinder of FIG. 8.

Referring to FIG. 9, the rotating grinder 120 may include a center body 121.

The center body 121 may be positioned at a center of the rotating grinder 120. The center body 121 may be installed at a center of the grinding case 110.

The center body 121 may be connected to the power transfer member 150 and receive power generated by the driver 70 and transferred to the power transfer member 150.

The center body 121 may be substantially formed in a shape of a truncated cone having a wider cross section at the lower portion. Because a lower portion of the center body 121 is wider than an upper portion of the center body 121, the center body 121 may more stably support the rotating grinder 120 rotating. However, the shape of the center body 121 is not limited to the truncated cone.

The rotating grinder 120 may include a first blade 122.

The first blade 122 may extend toward a side wall 111 of the grinding case 110 from the center body 121. The first blade 122 may include a connecting portion 1221, a first grinding portion 1223, and a second grinding portion 1222.

The first grinding portion 1223 may extend in parallel to the side wall 111 of the grinding case 110. More specifically, the first grinding portion 1223 may extend substantially in a vertical direction.

The second grinding portion 1222 may be connected to the first grinding portion 1223. The second grinding portion 1222 may extend horizontally with respect to the bottom plate 112 of the grinding case 110. The second grinding portion 1222 may be substantially perpendicular to the first grinding portion 1223.

The connecting portion 1221 may be connected to the second grinding portion 1222. One end of the connecting portion 1221 may be connected to the second grinding portion 1222, and the other end of the connecting portion 1221 may be connected to the center body 121.

Because the first blade 122 rotates at a higher location than a second blade 123 and a third blade 124 which will be described below, the connecting portion 1221 may extend in such a way as to be inclined upward.

The rotating grinder 120 may include the second blade 123.

The second blade 123 may be curved and extend toward the side wall 111 of the grinding case 110 from the center body 121.

The second blade 123 may include a blade chamfer 1231 inclined with respect to a rotation direction of the rotating grinder 120.

In other words, the blade chamfer 1231 may be provided as a surface inclined with respect to the bottom plate 112 of the grinding case 110.

The second blade 123 may be formed at a lower height than the first blade 122.

The rotating grinder 120 may include the third blade 124.

The third blade 124 may include a curve portion 1241 curved from an outer circumferential surface of the center body 121 and extending toward the side wall 111 of the grinding case 110.

The third blade 124 may include an extension portion 1242 connected to the curve portion 1241 and extending straightly toward the side wall 111 of the grinding case 110.

Also, the third blade 124 may include an uneven portion 1243 formed at a lower side of the extension portion 1242 and having an uneven shape to rake out food waste existing on the bottom plate 112 of the grinding case 110.

The uneven portion 1243 of the third blade 124 may be formed in the lower side of the third blade 124 toward the bottom plate 112 of the grinding case 110.

The third blade 124 may be in contact with the bottom plate 112 of the grinding case 110. Accordingly, the third blade 124 may transfer grinded food waste stacked on the bottom plate 112 of the grinding case 110 through the outlet 114. Details about this will be described below.

Figure 10:
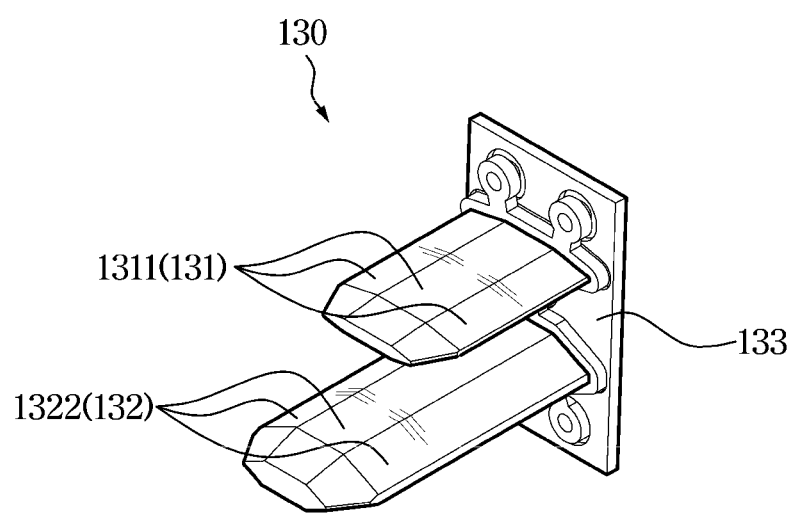
FIG. 10 shows a wall grinder of the grinder of FIG. 8.

FIG. 10 shows a wall grinder of the grinder of FIG. 8.

Referring to FIG. 10, the wall grinder 130 may include an installing body 133 coupled with an outer side of the grinding case 110.

The installing body 133 may be provided as a rectangular flat plate. The installing body 133 may be positioned on an outer side of the side wall 111 of the grinding case 110. The wall grinder 130 may penetrate the side wall 111 of the grinding case 110 and protrude to the inside of the grinding case 110.

More specifically, a first protrusion 131 and a second protrusion 132 of the wall grinder 130 may protrude to the inside of the grinding case 110.

The wall grinder 130 may include the first protrusion 131 and the second protrusion 132 extending from the installing body 133 toward the inside of the grinding case 110.

The first protrusion 131 may include a first chamfer 1311. A plurality of first chamfers 1311 may be formed. The second protrusion 132 may also include a second chamfer 1322. A plurality of second chamfers 1322 may be formed.

The second protrusion 132 may be longer than the first protrusion 131. More specifically, the second protrusion 132 may extend inward from the installing body 133 in such a way as to be longer than the first protrusion 131.

Figure 11:
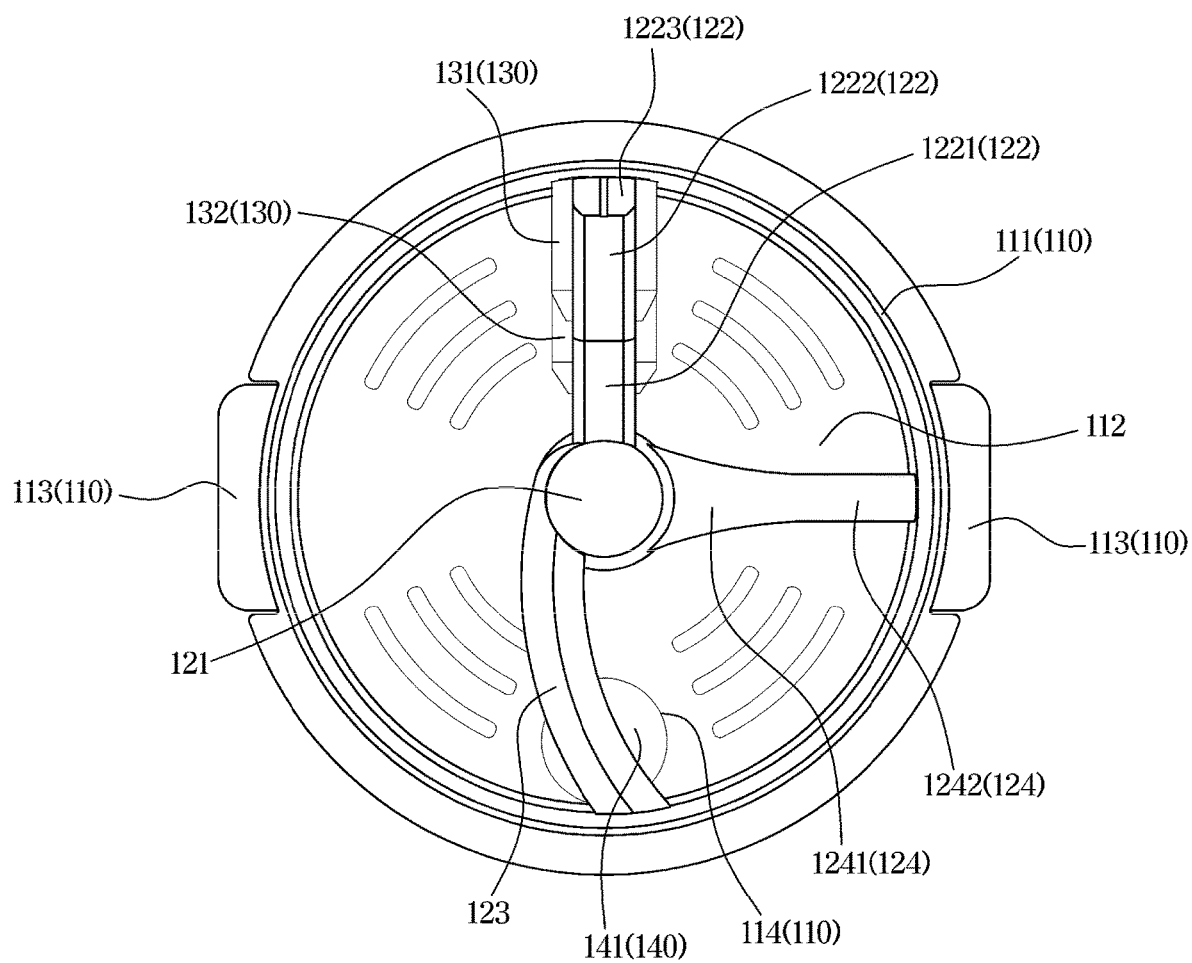
FIG. 11 is a top view of the grinder in the food waste disposer of FIG. 6.

FIG. 11 is a top view of the grinder in the food waste disposer of FIG. 6.

The grinding case 110 may include the side wall 111 formed in a circle shape. The grinding case 110 may include the bottom plate 112 forming a bottom of the grinding case 110. Also, the grinding case 110 may include the outlet 114 formed in the bottom plate 112.

The side wall 111 of the grinding case 110 may form the inner and outer surfaces of the grinding case 110. The wall grinder 130 described above may penetrate the side wall 111 of the grinding case 110 and mounted on the side wall 111.

In the bottom plate 112 of the grinding case 110, an uneven structure may be formed to grind food waste by interworking with the uneven portion 1243 of the third blade 124, although not limited thereto. However, the bottom plate 112 of the grinding case 110 may have a smooth surface.

The rotating grinder 120 may be spaced a preset distance from the side wall 111 of the grinding case 110.

More specifically, an end of the first blade 122 of the rotating grinder 120 may be spaced a preset distance from the side wall 111 of the grinding case 110. In other words, the first grinding portion 1223 of the first blade 122 may extend in parallel to the side wall 111 of the grinding case 110 without being in contact with the side wall 111.

An end of the second blade 123 may be spaced a preset distance from the side wall 111 of the grinding case 110. Also, an end of the third blade 124 may be spaced a preset distance from the side wall 111 of the grinding case 110.

In a case in which the rotating grinder 120 rotates in a state in which an end of the rotating grinder 120 is in close contact with the grinding case 110, a gap may be made between the rotating grinder 120 and the grinding case 110, and food waste may be stuck in the gap.

Also, due to friction between the grinding case 110 and the rotating grinder 120, noise may be generated and components may be damaged.

Accordingly, because the end of the rotating grinder 120 of the food waste disposer 1 according to various embodiments of the disclosure is spaced a preset distance from the side wall 111 of the grinding case 110, food waste may be prevented from being stuck between the side wall 111 and the rotating grinder 120 and the rotating grinder 120 may be driven with lower noise. Also, the rotating grinder 120 and the grinding case 110 may secure a longer durability.

Figure 12:
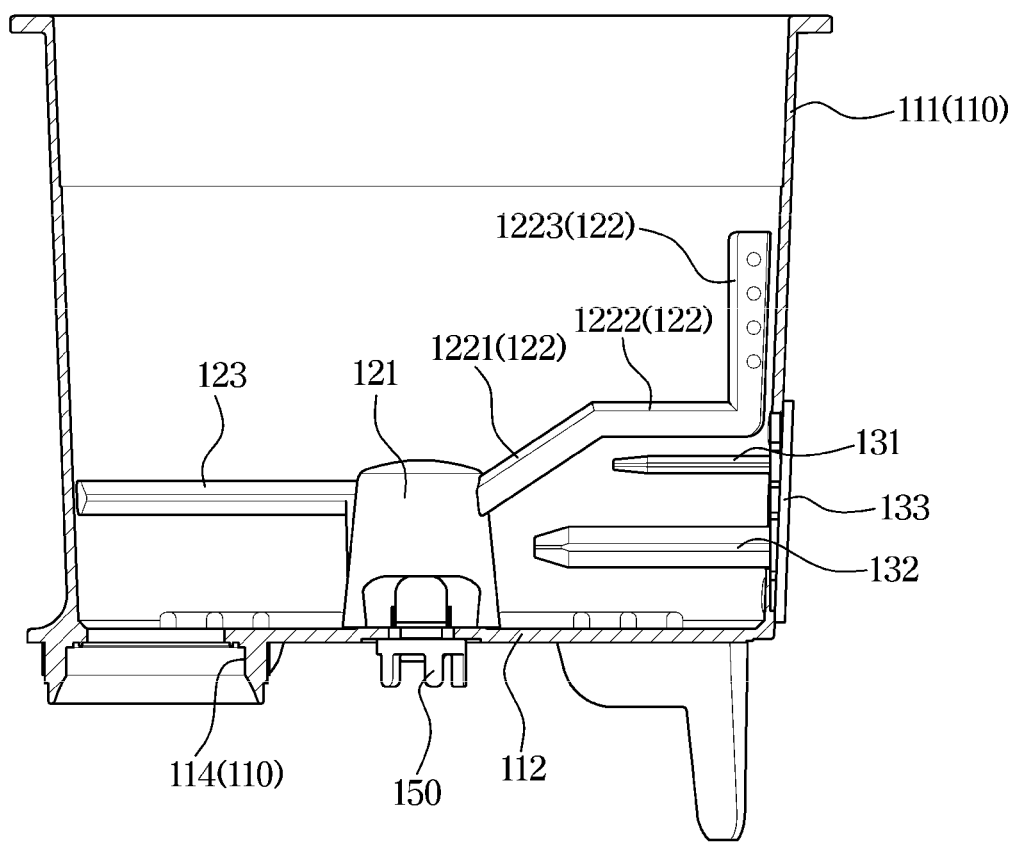
FIG. 12 is a cross-sectional view showing a state in which a first blade passes through a wall grinder in a food waste disposer according to various embodiments of the disclosure.
Figure 13:
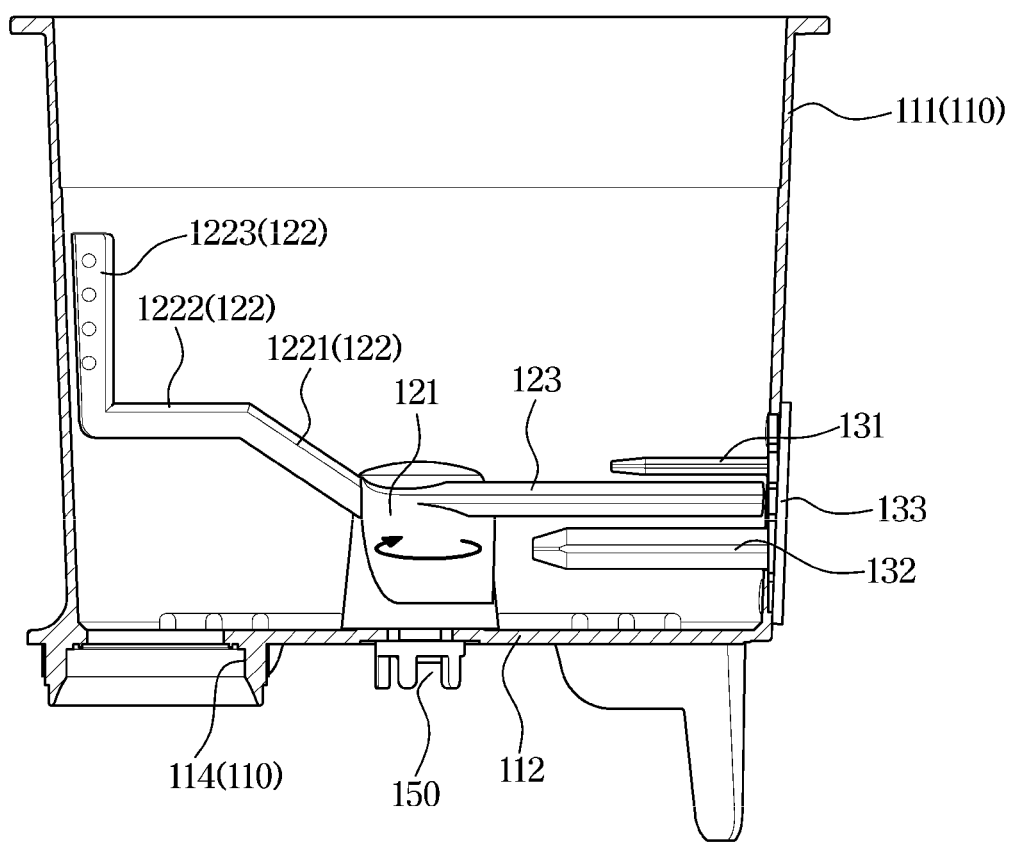
FIG. 13 is a cross-sectional view showing a state in which a second blade passes through a wall grinder in a food waste disposer according to various embodiments of the disclosure.
Figure 14:
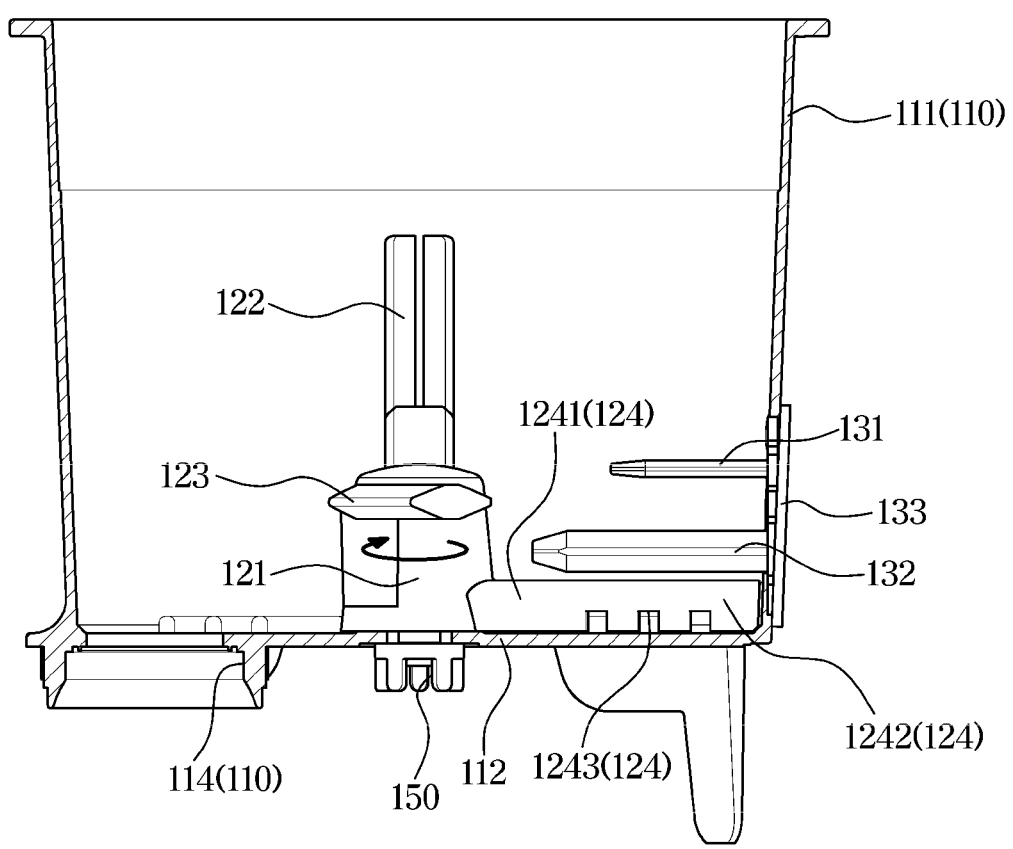
FIG. 14 is a cross-sectional view showing a state in which a third blade passes through a wall grinder in a food waste disposer according to various embodiments of the disclosure.

FIG. 12 is a cross-sectional view showing a state in which a first blade passes through a wall grinder in a food waste disposer according to various embodiments of the disclosure. FIG. 13 is a cross-sectional view showing a state in which a second blade passes through a wall grinder in a food waste disposer according to various embodiments of the disclosure. FIG. 14 is a cross-sectional view showing a state in which a third blade passes through a wall grinder in a food waste disposer according to various embodiments of the disclosure.

A process of processing food waste through interworking between the rotating grinder 120 and the wall grinder 130 of the food waste disposer 1 according to various embodiments of the disclosure will be described with reference to FIGS. 12 to 14.

Referring to FIG. 12, according to a rotation of the rotating grinder 120, the first blade 122 may be positioned above the first protrusion 131 of the wall grinder 130. The first grinding portion 1223 of the first blade 122 may extend in parallel to the side wall 111 of the grinding case 110.

The connecting portion 1221 of the first blade 122 may stir food waste existing inside the grinding case 110.

Also, the first grinding portion 1223 of the first blade 122 may grind food waste rotated and collected on the side wall 111 of the grinding case 110 and separate the food waste from the side wall 111 of the grinding case 110.

The second grinding portion 1222 of the first blade 122 may rotate to face an upper surface of the first protrusion 131 of the wall grinder 130.

At this time, because the first protrusion 131 includes the first chamfer 1311, food waste stuck between the first protrusion 131 and the second grinding portion 1222 of the first blade 122 may be more smoothly grinded.

Because the first chamfer 1311 is formed in the first protrusion 131, the first protrusion 131 may secure a wider surface in contact with food waste. A single first chamfer 1311 or a plurality of first chamfers 1311 may be formed.

Referring to FIG. 13, the second blade 123 may be positioned between the first protrusion 131 and the second protrusion 132 of the wall grinder 130 according to a rotation of the rotating grinder 120.

The second blade 123 may include the blade chamfer 1231, and the first protrusion 131 and the second protrusion 132 may include the first chamfer 1311 and the second chamfer 1322, respectively.

Accordingly, food waste existing between an upper portion of the second blade 123 and a lower portion of the first protrusion 131 may be grinded, and food waste existing between a lower portion of the second blade 123 and the upper portion of the second protrusion 132 may be grinded.

The blade chamfer 1231, the first chamfer 1311, and the second chamfer 1322 may increase areas where food waste is in contact with the second blade 123, the first protrusion 131, and the second protrusion 132, thereby improving grinding performance.

Also, because the second blade 123 is curved along a rotation direction of the rotating grinder 120, the second blade 123 may more smoothly stir food waste.

Simultaneously, the first blade 122 may grind food waste stacked on the inner surface of the grinding case 110 at the opposite side of the side wall 111 on which the wall grinder 120 is installed, and separate the food waste from the side wall 111.

Referring to FIG. 14, the third blade 124 may be positioned below the second protrusion 132 of the wall grinder 130 according to a rotation of the rotating grinder 120.

The third blade 124 may include the curve portion 1241 connected to the center body 121, and the extension portion 1242 connected to the curve portion 1241 and forming an end of the third blade 124.

Because the uneven portion 1243 is formed at the lower side of the extension portion 1242, the third blade 124 may rake out food waste stacked on the bottom plate 112 of the grinding case 110 and separate the food waste from the bottom plate 112. Also, the third blade 124 may perform finer grinding.

Also, the curve portion 1241 of the third blade 124 may be curved from a tangential direction to the center body 121. Accordingly, the curve portion 1241 may more stably receive a rotation force of the center body 121 to more finely grind and rake out food waste stacked on the bottom plate 112.

Accordingly, the food waste disposer 1 according to various embodiments of the disclosure may more finely grind food waste existing inside the grinding case 110 through interworking of the rotating grinder 120 and the wall grinder 130.

Also, by efficiently designing a layout of internal configurations of the food waste disposer 1, a more compact size of the food waste disposer 1 may be secured.

By arranging components of the food waste disposer to secure a compact size of the food waste disposer, ease of use may increase.

By preventing food waste from clumping together on the inner wall of the grinding case to uniformly stir and grind the food waste, the driving motor may be prevented from overloading.

By forming chamfers at some portions of the rotating grinder and the wall grinder, food waste grinding performance may be improved.

Although a few embodiments of the disclosure have been shown and described, it would be appreciated by those skilled in the art that changes may be made in these embodiments without departing from the principles and spirit of the disclosure, the scope of which is defined in the claims and their equivalents.

Although the present disclosure has been described with various embodiments, various changes and modifications may be suggested to one skilled in the art. It is intended that the present disclosure encompass such changes and modifications as fall within the scope of the appended claims.

What is claimed is:

1. A food waste disposer comprising:
    a housing;
    a grinder detachably installed inside the housing and configured to grind food waste accommodated therein; and
    a deodorizer positioned to a side of the grinder, and configured to suck a smell generated from the grinder and discharge the smell to outside of the housing,
    wherein the grinder comprises:
        a grinding case;
        a rotating grinder including a plurality of blades rotatably installed at different heights inside the grinding case; and
        a wall grinder including a protrusion protruding inward from the grinding case at a different height from the plurality of blades, the wall grinder detachably installed on a side wall of the grinding case, wherein the wall grinder includes a chamfer formed at an outer surface of the protrusion in such a way as to be inclined with respect to the outer surface of the protrusion.

2. The food waste disposer of claim 1, wherein the rotating grinder comprises:
    a center body installed at a center of the grinding case and receiving power; and
    a first blade extending toward the side wall of the grinding case from the center body, wherein the first blade includes a grinding portion extending in parallel to the side wall of the grinding case and configured to separate food waste stacked on the side wall.

3. The food waste disposer of claim 2, wherein:
    the grinding portion is a first grinding portion, and
    the first blade further includes a second grinding portion connected to the first grinding portion and extending horizontally with respect to a bottom plate of the grinding case.

4. The food waste disposer of claim 2, wherein the rotating grinder further comprises a second blade curved from the center body and extending toward the side wall of the grinding case.

5. The food waste disposer of claim 4, wherein the second blade comprises a blade chamfer inclined with respect to a rotation direction of the rotating grinder.

6. The food waste disposer of claim 2, wherein the rotating grinder comprises a third blade extending from the center body toward the side wall of the grinding case, and including an uneven portion formed at a lower side of the third blade to rake out food waste existing on a bottom plate of the grinding case.

7. The food waste disposer of claim 1, wherein the rotating grinder comprises:
    a first blade including a grinding portion extending in parallel to the side wall of the grinding case;
    a second blade curved and extending along a rotation direction of the rotating grinder; and
    a third blade formed at a lower location than the second blade.

8. The food waste disposer of claim 7, wherein the wall grinder comprises:
    a first protrusion positioned between the first blade and the second blade; and
    a second protrusion positioned between the second blade and the third blade.

9. The food waste disposer of claim 1, further comprising:
    an upper frame positioned in an upper portion of the housing and including an opening in which the grinder is inserted; and
    a housing cover rotatably coupled with one side of the upper frame and the housing cover is configured to open or close the opening.

10. The food waste disposer of claim 9, wherein the upper frame comprises:

a base forming an upper surface; and
an inlet protruding upward from the base and accommodating a portion of the deodorizer,
wherein a communicating hole communicating with the grinder is formed in the inlet.

11. The food waste disposer of claim 10, wherein the deodorizer comprises:
a communicating case that is partially accommodated in the inlet, the communicating case positioned behind the grinder; and
a fan installing case connected to the communicating case, and configured to accommodate a circulating fan forming a suction airflow toward the communicating case from the grinder.

12. The food waste disposer of claim 11, wherein the deodorizer comprises:
a filter configured to filter air sucked from the grinder; and
an exhaust case installed in a side of the filter and communicating with an exhaust hole of the housing, wherein air filtered by the filter flows along the exhaust case.

13. The food waste disposer of claim 9, further comprising:
a bottom frame positioned below the upper frame and on which the grinder is seated; and
a heater positioned between the bottom frame and the grinder, and configured to heat the grinder.

14. The food waste disposer of claim 1, further comprising a food waste bin positioned below the grinder to store food waste grinded by the grinder and transferred from the grinder.

15. A food waste disposer comprising:
a housing including an exhaust hole;
a grinder detachably installed inside the housing and configured to grind food waste accommodated therein;
a deodorizer positioned behind the grinder, and configured to suck a smell generated from the grinder and discharge the smell through the exhaust hole of the housing; and
an upper frame positioned in an upper portion of the housing and including:
an opening accommodating the grinder, and
an inlet accommodating a portion of the deodorizer,
wherein the grinder comprises:
a grinding case configured to accommodate food waste therein; and
a rotating grinder rotatably installed inside the grinding case, the rotating grinder includes:
a first blade in which a grinding portion extending in parallel to a side wall of the grinding case is formed to separate food waste from the side wall of the grinding case; and
a second blade formed at a lower height than the first blade; and
a wall grinder including a protrusion protruding inward from the grinding case at a different height from the plurality of blades, the wall grinder detachably installed on a side wall of the grinding case, wherein the wall grinder includes a chamfer formed at an outer surface of the protrusion in such a way as to be inclined with respect to the outer surface of the protrusion.

16. The food waste disposer of claim 15, wherein the rotating grinder further includes a third blade formed at a lower height than the second blade and including an uneven portion formed toward a bottom plate of the grinding case.

17. The food waste disposer of claim 16, further include a wall grinder detachably installed on the side wall of the grinding case, and including a protrusion formed at a different height from the first blade, the second blade, and the third blade and extending toward inside of the grinding case.

18. A food waste disposer comprising:
a housing including an opening formed in an upper portion thereof;
a housing cover configured to open or close an upper side of the housing;
a grinder configured to grind food waste, and including:
a grinding case installed through the opening of the housing,
a blade including a grinding portion extending in parallel to a side wall of the grinding case;
a deodorizer positioned behind the grinder, and configured to suck a smell generated from the grinder and filter the smell;
a food waste bin positioned below the grinder and configured to store food waste; and
a wall grinder including a protrusion protruding inward from the grinding case at a different height from the plurality of blades, the wall grinder detachably installed on a side wall of the grinding case, wherein the wall grinder includes a chamfer formed at an outer surface of the protrusion in such a way as to be inclined with respect to the outer surface of the protrusion.

19. The food waste disposer of claim 18, further comprising:
an opening formed in an upper portion of the housing and configured to accommodate the grinder, and
an upper frame formed to one side of the opening and including an inlet communicating the deodorizer with the grinder.

20. The food waste disposer of claim 18, wherein the grinding case further includes at least one handle configured to be gripped when separating the grinder from the housing through the opening of the housing.

* * * * *